(12) United States Patent
Fischer et al.

(10) Patent No.: US 6,284,932 B1
(45) Date of Patent: Sep. 4, 2001

(54) METHOD FOR PRODUCING ALCOHOLS CONTAINING CYCLOALIPHATIC GROUPS

(75) Inventors: Rolf Fischer, Heidelberg; Rolf Pinkos, Bad Dürkheim; Joachim Wulff-Döring, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,754

(22) PCT Filed: May 12, 1998

(86) PCT No.: PCT/EP98/02778

§ 371 Date: Nov. 15, 1999

§ 102(e) Date: Nov. 15, 1999

(87) PCT Pub. No.: WO98/52892

PCT Pub. Date: Nov. 26, 1998

(30) Foreign Application Priority Data

May 16, 1997 (DE) ............................................. 197 20 606

(51) Int. Cl.$^7$ .................................................. C07C 31/13
(52) U.S. Cl. ............................................. 568/831; 568/826
(58) Field of Search ....................................... 568/826, 831

(56) References Cited

U.S. PATENT DOCUMENTS

| 4,104,478 | 8/1978 | Trivedi | 568/885 |
| 4,317,918 | * 3/1982 | Tsksno | 568/826 |
| 5,395,986 | 3/1995 | Scarlett et al. | 568/831 |
| 6,140,545 | * 10/2000 | Merger | 568/831 |

FOREIGN PATENT DOCUMENTS

| 1320839 | 6/1973 | (GB) . |
| 52000242 | 1/1977 | (JP) . |
| 6228028 | 8/1994 | (JP) . |
| 8217707 | 8/1996 | (JP) . |

* cited by examiner

Primary Examiner—Michael L. Shippen
(74) Attorney, Agent, or Firm—Keil & Weinkauf

(57) ABSTRACT

In a process for preparing alcohols containing cycloaliphatic groups by hydrogenation of carboxylic acids containing aromatic nuclei, or anhydrides or esters thereof, in the presence of a catalyst, the hydrogenation is carried out in one stage, and the catalyst contains at least one element from groups 8 to 10 and at least one element from group 7 of the Periodic Table of the Elements, in the form of the metal or an oxide in each case.

8 Claims, No Drawings

METHOD FOR PRODUCING ALCOHOLS CONTAINING CYCLOALIPHATIC GROUPS

The invention relates to a process for preparing alcohols containing cycloaliphatic groups by hydrogenation of carboxylic acids containing aromatic nuclei, or anhy-drides or esters thereof, in the presence of a catalyst.

Processes for hydrogenating aromatic carboxylic acids to give cycloaliphatic alcohols are known. In these there is initial hydrogenation of the aromatic nucleus to the cycloaliphatic group, and then each carboxyl group is converted into a hydroxymethylene group.

JP-A 77/000242 (1977) describes a process for preparing 1,4-cyclohexanedimethanol. In this there is initial nuclear hydrogenation of terephthalic acid on a catalyst composed of 5% rhodium on carbon. The carboxyl groups are then converted into the alcohol groups by hydrogenation on a copper/chromium catalyst. The conversion can also be carried out in a reactor which is operated continuously and which contains the two catalysts spatially separated from one another in sequence.

JP-A 06/228028 (1994) describes a process for preparing 1,4-cyclohexanedimethanol in which there is initially hydrogenation of the aromatic nucleus of terephthalic acid on a catalyst composed of 5% Ru on $A_2O_3$, and the resulting compound is then hydrogenated on a supported catalyst which contains Ru and/or Rh and Sn to give 1,4-cyclohexanedimethanol.

U.S. Pat. No. 5,395,986 describes a process in which the cycloaliphatic dicarboxylic acid resulting from nuclear hydrogenation is hydrogenated on a copper/chromium catalyst to give 1,4-cyclohexanedimethanol.

Two-stage processes are elaborate to carry out and are costly inter alia owing to the use of two different catalysts in two reaction stages.

It is an object of the present invention to provide a process for the catalytic hydrogenation of carboxylic acids containing aromatic nuclei to alcohols containing cycloaliphatic groups which avoids the disadvantages of known methods.

We have found that this object is achieved by providing a process for preparing alcohols containing cycloaliphatic groups by hydrogenation of carboxylic acids containing aromatic nuclei, or anhydrides or esters thereof, in the presence of a catalyst, where the hydrogenation is carried out in one stage and the catalyst contains at least one element from the group consisting of Pd, Ru and Pt and the element Re in the form of the metal or an oxide in each case.

We have found that the hydrogenation can be carried out in one stage when specific catalysts containing at least two metals or two metal oxides are used.

The catalyst can be employed as unsupported or supported catalyst for this purpose. All known carrier materials are suitable for use as supported catalyst, for example active carbons, $SiO_2$, $Al_2O_3$, $TiO_2$, $ZrO_2$, clays such as montmorillonites, zeolites or mixtures thereof. The catalyst is preferably employed as unsupported catalyst.

It is possible, for example, to employ a catalyst which can be prepared by reducing an aqueous suspension and/or solution of oxides, oxide hydrates, carbonates, nitrates, carboxylates, chelates, sulfates, phosphates and/or halides of the elements employed.

The catalyst preferably contains one element from the group consisting of Pd, Ru or Pt, preferably Pt.

The element from group 7 of the Periodic Table of the Elements which is preferably used is Re.

The catalyst preferably additionally contains at least one other element from one of groups 3 and 5 to 12 and 14 and the lanthanides of the Periodic Table of the Elements (group IVa or group Ib, IIb, IIIb, Vb, VIb, VIIb or VIII of the Periodic Table of the Elements or of the lanthanides) in the form of the metal or an oxide.

Preferred examples of the at least one other element are Sn, V, Cr, Mo, W, Mn, Fe, Ru, Os, Co, Ni, Pd, Cu, Ag, Au, Zn, La and Ce. The elements can be employed as oxides, oxide hydrates, carbonates, nitrates, carboxylates, chelates of 1,3-diketo compounds, sulfates, phosphates or halides. The elements Re and Pd, Ru and Pt are preferably employed as oxides, oxide hydrates, carbonates, nitrates, sulfates, halides, borides, carboxylates such as acetates, chelates of 1,3-diketo compounds such as enolates of acetylacetonate or benzylacetonate. Oxides and oxide hydrates are particularly preferred, such as $RuO_2$, $PdO_2$, $PtO_2$ and $Re_2O_7$.

The catalyst particularly preferably contains of an element from the group consisting of Pd, Ru and Pt, and the element Re and at least one element from group 11 of the Periodic Table of the Elements in the form of the metal or an oxide. In particular, the catalyst contains Pd, Ru or Pt in addition to Re and Ag, Mo or Au in the form of the metal or an oxide. The catalyst may contain the abovementioned elements or consist of them. It preferably consists of these elements in the form of the metal or an oxide in each case.

The catalysts employed according to the invention can be prepared by mixing the appropriate compounds of the elements and reducing, preferably with hydrogen. However, the reduction can also be carried out sequentially. For example, $PtO_2$, an Re compound and, where appropriate, a compound of at least one other element are introduced into water and reduced with hydrogen. In this case, the reduction is preferably carried out at from 100 to 700° C., particularly preferably 200 to 600° C., in particular 250 to 500° C. The catalysts obtained in this way can be employed for the hydrogenation immediately after the reduction. Supported catalysts can be prepared, for example, in such a way that a Pt component, preferably Pt oxide or Pt oxide hydrate, is already present on the carrier, it being possible to prepare the Pt/carrier mixture by impregnation or joint precipitation of Pt oxide precursor or Pt oxide hydrate precursor and carrier material and subsequent calcination. The Re compound and the at least one other element can be added by impregnation or precipitation. It is moreover possible for the Pt oxide or Pt oxide hydrate to have been reduced on the carrier previously. Following the above preparation conditions, the catalysts are in the form of mixtures of the elements or, partly or predominantly, as intermetallic compounds.

The ratio by weight of Pt to Re or of Pt to the other element which may be present is preferably 100–0.01, particularly preferably 50–0.05, in particular 10–0.1.

The carboxylic acid which can be employed in the hydrogenation is any carboxylic acid containing aromatic nuclei, or its anhydride or esters. The carboxylic acid may moreover have any number of carboxyl groups. As a rule, it contains from 1 to 3 carboxyl groups. It is, in particular, a dicarboxylic acid. The carboxyl groups can be separated from the aromatic nucleus by an alkylene radical. In this case, the alkylene radical preferably contains from 1 to 5 carbon atoms. It is particularly preferably an aromatic carboxylic acid in which the carboxyl groups are directly bonded to the aromatic nucleus. Aromatic nuclei to be considered are all suitable aromatic nuclei such as benzene nuclei, naphthalene nuclei and more highly fused aromatic nuclei. The aromatic nucleus is preferably a benzene nucleus. The aromatic nucleus may be substituted by hydroxyl groups, $C_{1-12}$-alkyl radicals, $C_{1-12}$-alkoxy radicals or $C_{1-12}$-hydroxyalkyl radicals. If carbonyl functionalities are present in the molecule or in the substituents, these are also reduced in the hydrogenation. If carbon double or triple bonds are present in the substituents, these are also reduced to the corresponding saturated compounds.

Examples of suitable carboxylic acids are monocarboxylic acids such as benzoic acid or dicarboxylic acids such as phthalic acid or terephthalic acid. Examples of esters which can be employed are the methyl, ethyl, propyl or butyl esters. The carboxylic acids can also be employed as anhydrides, for example phthalic anhydride. The resulting alcohols can be employed in a large number of applications, for example as intermediates or alcohol components for preparing polymers.

Terephthalic acid and its esters are preferably employed.

The carboxylic acids or anhydrides or esters thereof can be employed undiluted or as suspension or solution. Suitable solvents are all substances which are inert under the reaction conditions, such as water, dioxane, tetrahydrofuran, ethylene glycol ethers, hydrocarbons such as hexane or alcohols such as methanol, ethanol, propanol, butanol or the reaction product itself Preferably employed as solvents are water and the alcohols produced in the reaction.

The hydrogenation is carried out in one stage, ie. aromatic nuclei and carboxyl groups are simultaneously hydrogenated on the catalyst.

This hydrogenation is preferably carried out at from 30 to 300° C., particularly preferably 80 to 215° C., in particular 100 to 190° C. The pressure is preferably from 1 to 350 bar. The pressure for reactions in the gas phase is preferably from 1 to 80 bar, and for reactions in the liquid phase is preferably from 20 to 330 bar, particularly preferably 100 to 300 bar.

The hydrogenation can be carried out continuously or batchwise. The catalyst can be employed in a form suitable for the way the reaction is carried out. If the process is carried out batchwise, the catalyst may be employed, for example, in the form of a powder in suspension. If the process is carried out continuously, the catalyst may be arranged as a fixed bed for reaction in the liquid or gas phase. The hydrogenation can moreover be operated with or without product recycling.

If the reaction is carried out continuously, it is also possible to employ a sequence of reactors. This may be necessary, for example, to improve dissipation of the heat of reaction.

The invention is explained in detail by the following examples.

EXAMPLES

Example 1

0.1 g of $PtO_2$, 0.2 g of $Re_2O_7$, 0.1 g of silver acetate and 9 g of water were introduced into a metal autoclave. Then 60 bar of hydrogen were injected, and the mixture was heated to 270° C. with stirring. After one hour, it was cooled to room temperature, the autoclave was decompressed, and 1 g of terephthalic acid was added. Then 100 bar of hydrogen were injected, and the mixture was heated to 150° C. with stirring. After 2 hours, cooling and decompression were again carried out. The discharge from the reaction was analyzed by gas chromatography. 83% 1,4-cyclohexanedimethanol were found, with complete conversion. The remainder consisted mainly of 4-hydroxymethylcyclohexanecarboxylic acid and 4-methylhydroxymethylcyclohexane.

Example 2

0.1 g of $PtO_2$ and 0.2 g of $Re_2O_7$ were employed as in Example 1. The hydrogenation at 150° C. took place for one hour. The discharge contained 71% 1,4-cyclohexanedimethanol. The remainder consisted mainly of 4-hydroxymethylcyclohexanecarboxylic acid, 4-formylhydroxymethylcyclohexane and 4-methylhydroxymethylcyclohexane.

We claim:

1. A process for preparing alcohols containing cycloaliphatic groups by hydrogenation of carboxylic acids containing aromatic nuclei, or anhydrides or esters thereof, in the presence of a catalyst, wherein the hydrogenation is carried out in one stage, and the catalyst contains at least one element from the group consisting of Pd, Ru and Pt and the element Re in the form of the metal or an oxide in each case.

2. A process as claimed in claim 1, wherein the catalyst additionally contains at least one other element from one of groups 3 and 5 to 12 and 14 and the lanthanides of the Periodic Table of the Elements in the form of the metal or an oxide.

3. A process as claimed in claim 1, wherein the catalyst contains at least one element from group 11 of the Periodic Table of the Elements in the form of the metal or an oxide in each case.

4. A process as claimed in claim 1, wherein the catalyst contains as other element Ag, Mo or Au, in the form of the metal or an oxide in each case.

5. A process as claimed in claim 1, wherein an aromatic carboxylic acid is hydrogenated to give a cycloaliphatic alcohol.

6. A process as claimed in claim 1, wherein the carboxylic acid is terephthalic acid.

7. A process as claimed in claim 1, wherein the hydrogenation temperature does not exceed 200° C.

8. A process as claimed in claim 1, wherein the hydrogenation is carried out in the presence of water.

* * * * *